(12) United States Patent
Khan

(10) Patent No.: US 6,855,243 B2
(45) Date of Patent: Feb. 15, 2005

(54) ELECTROCHEMICAL TEST STRIP HAVING A PLURALITY OF REACTION CHAMBERS AND METHODS FOR USING THE SAME

(75) Inventor: Tahir S. Khan, San Jose, CA (US)

(73) Assignee: LifeScan, Inc., Milpitas, CA (US)

(*) Notice: Subject to any disclaimer, the term of this patent is extended or adjusted under 35 U.S.C. 154(b) by 289 days.

(21) Appl. No.: 09/844,929

(22) Filed: Apr. 27, 2001

(65) Prior Publication Data

US 2004/0217016 A1 Nov. 4, 2004

(51) Int. Cl.[7] .................. G01N 27/327; G01N 27/333
(52) U.S. Cl. .................... 205/777.5; 205/792; 204/409; 204/403.14; 204/411
(58) Field of Search ............... 204/403.01, 403.03, 204/403.04, 403.14, 409, 411, 412; 205/777.5, 775, 792

(56) References Cited

U.S. PATENT DOCUMENTS

| | | | |
|---|---|---|---|
| 5,004,583 A | * 4/1991 | Guruswamy et al. | 204/401 |
| 5,269,891 A | 12/1993 | Colin | 204/153.12 |
| 5,421,981 A | * 6/1995 | Leader et al. | 204/403.13 |
| 5,672,256 A | * 9/1997 | Yee | 204/403.14 |
| 5,830,170 A | 11/1998 | Whiteman et al. | 604/1 |
| 5,834,224 A | 11/1998 | Ruger et al. | 435/14 |
| 5,942,102 A | 8/1999 | Hodges et al. | 205/775 |
| 5,972,199 A | 10/1999 | Heller et al. | 205/777.5 |
| 6,123,820 A | * 9/2000 | Bergkuist et al. | 204/409 |
| 6,325,917 B1 | * 12/2001 | Maxwell et al. | 205/777.5 |
| 6,413,410 B1 | * 7/2002 | Hodges et al. | 205/775 |

FOREIGN PATENT DOCUMENTS

| | | |
|---|---|---|
| EP | 1167538 A1 * | 6/2000 |
| EP | 1195441 A | 4/2002 |
| GB | 2 284 892 | 6/1995 |
| GB | 2 304 628 | 3/1997 |
| US | 6020110 | 2/2000 |
| WO | 97/18464 A1 * | 5/1997 ......... G01N/27/403 |
| WO | WO 97/18465 | 5/1997 |
| WO | WO 99/49307 | 9/1999 |
| WO | WO 00 28068 | 5/2000 |
| WO | WO 01 57510 A | 8/2001 |
| WO | WO 0250609 A | 6/2002 |

OTHER PUBLICATIONS

English language translation of Schibli (EP 1167538 A1).*
Derwent abstract of Schibli (EP 1167538 A1).*
Database WPI, Sec. Ch. Week 198903, Derwent Pub. XP002224773 & SU 1 408 300 A.
Dalmia et al, J. Electroanalytical Chemistry (1997) 430: 205–214.
Nakashima et al., J. Chem. Soc. (1990) 12: 845–847.
Palacin et al., Chem. Mater. (1996) 8:1316–1325.

* cited by examiner

*Primary Examiner*—Alex Noguerola
(74) *Attorney, Agent, or Firm*—Susan C. Tall; Bret E. Field; Bozicevic Field & Francis, LLP

(57) ABSTRACT

Electrochemical test strips and methods for their use in the detection of an analyte in a physiological sample are provided. The subject test strips have a plurality of reaction zones defined by opposing metal electrodes separated by a thin spacer layer. The reagent compositions present in each reaction zone may be the same or different. In addition, each reaction zone may have a separate fluid ingress channel, or two or more of the reaction zones may have fluid ingress channels that merge into a single channel. The subject electrochemical test strips find application in the detection of a wide variety of analytes, and are particularly suited for use the detection of glucose.

34 Claims, 2 Drawing Sheets

ELECTROCHEMICAL TEST STRIP HAVING A PLURALITY OF REACTION CHAMBERS AND METHODS FOR USING THE SAME

FIELD OF THE INVENTION

The field of this invention is analyte determination, particularly electrochemical analyte determination and more particularly the electrochemical determination of blood analytes.

BACKGROUND

Analyte detection in physiological fluids, e.g. blood or blood derived products, is of ever increasing importance to today's society. Analyte detection assays find use in a variety of applications, including clinical laboratory testing, home testing, etc., where the results of such testing play a prominent role in diagnosis and management in a variety of disease conditions. Analytes of interest include glucose for diabetes management, cholesterol, and the like. In response to this growing importance of analyte detection, a variety of analyte detection protocols and devices for both clinical and home use have been developed.

One type of method that is employed for analyte detection is an electrochemical method. In such methods, an aqueous liquid sample is placed into a reaction zone in an electrochemical cell comprising two electrodes, i.e. a reference and working electrode, where the electrodes have an impedance which renders them suitable for amperometric measurement. The component to be analyzed is allowed to react directly with an electrode, or directly or indirectly with a redox reagent to form an oxidizable (or reducible) substance in an amount corresponding to the concentration of the component to be analyzed, i.e. analyte. The quantity of the oxidizable (or reducible) substance present is then estimated electrochemically and related to the amount of analyte present in the initial sample.

Because of the broad applicability of electrochemical based detection protocols, there continues to be interest in the identification of new devices and methods in this area.

Relevant Literature

U.S. Patent documents of interest include: U.S. Pat. Nos. 5,269,891; 5,830,170; 5,834,224; 5,942,102 and 5,972,199. Other patent documents of interest include WO 99/49307; WO 97/18465 and GB 2 304 628. Other references of interest include: Dalmia et al, J. Electroanalytical Chemistry (1997) 430: 205–214; Nakashima et al., J. Chem. Soc. (1990) 12: 845–847; and Palacin et al., Chem. Mater. (1996) 8:1316–1325.

SUMMARY OF THE INVENTION

Electrochemical test strips and methods for their use in the detection of an analyte in a physiological sample are provided. The subject test strips have a plurality of reaction zones defined by opposing metal electrodes separated by a thin spacer layer. The reagent compositions present in each reaction zone may be the same or different. In addition, each reaction zone may have a separate fluid ingress channel, or two or more of the reaction zones may have fluid ingress channels that merge into a single channel. The subject electrochemical test strips find application in the detection of a wide variety of analytes, and are particularly suited for use in the detection of glucose.

DESCRIPTION OF THE SPECIFIC EMBODIMENTS

Electrochemical test strips and methods for their use in the detection of an analyte in a physiological sample are provided. The subject test strips have a plurality of reaction zones defined by opposing metal electrodes separated by a thin spacer layer. The reagent compositions present in each reaction zone may be the same or different. In addition, each reaction zone may have a separate fluid ingress channel, or two or more of the reaction zones may have fluid ingress channels that merge into a single channel. The subject electrochemical test strips find application in the detection of a wide variety of analytes, and are particularly suited for use in the detection of glucose.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, singular references include the plural, unless the context clearly dictates otherwise. Unless defined otherwise, all technical and scientific terms used herein have the same meaning as commonly understood to one of ordinary skill in the art to which this invention belongs.

Electrochemical Test Strips

Figure 1:
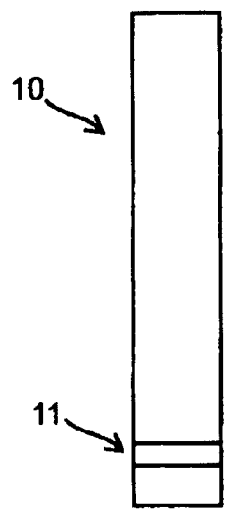
FIG. 1 provides a representation of an electrochemical test strip according to the prior art.
Figure 2:
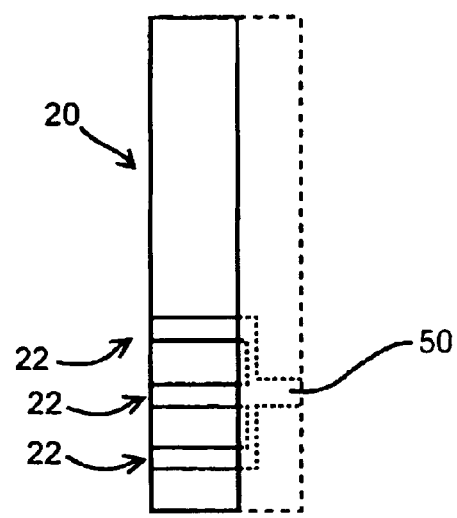
FIGS. 2 to 4 provide a representation of an electrochemical test strip according to the subject invention.

As summarized above, the electrochemical test strips of the subject invention are characterized by having a plurality of reaction zones. More specifically, the subject electrochemical test strips are made up of two opposing metal electrodes separated by a thin spacer layer, where these components define a plurality of distinct reaction areas or zones, i.e., chambers, in which is located a reagent system. As the subject electrochemical test strips have a plurality of reaction zones, they include at least 2 different reaction zones, and in certain embodiments at least 3 to 5 different reaction zones. The number of different reaction zones in electrochemical test strips according to the subject invention generally ranges from about 2 to 25, usually from about 2 to 15 and more usually from about 2 to 10 in many embodiments. While the different reaction zones of the test strips may, in general, be arranged in any convenient manner on the test strip, in many embodiments they are arranged in parallel and proximal to one end of the strip, as shown in the representative FIG. 2. In FIG. 2, electrochemical test strip 20 has a plurality of reaction zones, shown as channels, 22. This is in contrast to prior art electrochemical test strips as shown in FIG. 1 that have a single reaction zone 11.

As summarized above, the subject test strips are made up of a working electrode and reference electrode separated by spacer layer that is configured to define the plurality of reaction zones or areas of the subject strips. Each of the above elements, i.e. the working and reference electrodes, the spacer layer and the reaction area are now described separately in greater detail.

Electrodes

As indicated above, the subject electrochemical test strips include a working electrode and a reference electrode.

Generally, the working and reference electrodes are configured in the form of elongated rectangular strips. Typically, the length of the electrodes ranges from about 1.9 to 5.5 cm, usually from about 2 to 4.0 cm. The width of the electrodes ranges from about 0.20 to 0. 1.0 cm, usually from about 0.31 to 0.67 cm. The electrodes typically have metal thickness ranging from about 10 to 300 nm and usually from about 13 to 60 nm.

The working and reference electrodes are further characterized in that at least the surface of the electrodes that faces the reaction area in the strip is a metal, where metals of interest include palladium, gold, platinum, silver, iridium, carbon, doped indium tin oxide, stainless steel, nichrome and the like. In many embodiments, the metal is gold or palladium. While in principle the entire electrode may be made of the metal, each of the electrodes is generally made up of an inert support material on the surface of which is present a thin layer of the metal component of the electrode. In these more common embodiments, the thickness of the inert backing material typically ranges from about 51 to 356 $\mu$m, usually from about 25 to 254 $\mu$m while the thickness of the metal layer typically ranges from about 10 to 150 nm and usually from about 15 to 60 nm, e.g. a sputtered metal layer. Any convenient inert backing material may be employed in the subject electrodes, where typically the material is a rigid material that is capable of providing structural support to the electrode and, in turn, the electrochemical test strip as a whole. Suitable materials that may be employed as the backing substrate include plastics, e.g. PET, PETG, polyimide, polycarbonate, polystyrene, silicon, ceramic, glass, and the like.

The working and reference electrodes as described above may be fabricated using any convenient protocol. A representative protocol includes preparation of the metal electrodes by first sputtering the metal layer of sufficient thickness onto the surface of the inert backing material.

Spacer Layer

A feature of the subject electrochemical test strips is that the working and reference electrodes as described above face each other and are separated by only a short distance, such that the distance between the working and reference electrode in the reaction zone or area of the electrochemical test strip is extremely small. This minimal spacing of the working and reference electrodes in the subject test strips is a result of the presence of a thin spacer layer positioned or sandwiched between the working and reference electrodes. The thickness of this spacer layer generally ranges from about 12 to 500 $\mu$m, usually from about 50 to 153 $\mu$m.

Figure 3:
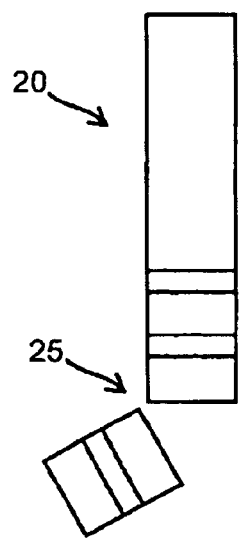
Figure 4:
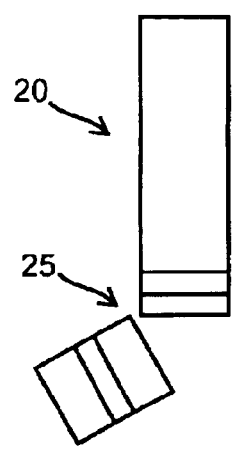

A feature of the subject strips is that the spacer layer is cut so as to provide a plurality of reaction zones or areas as described above, where each reaction area has at least an inlet port or ingress channel into the reaction zone, and generally an outlet port or egress channel out of the reaction zone as well, which channels provide for fluid communication between the interior of the reactions zones and the external environment of the strip. While the spacer layer of the strips shown in FIGS. 2 to 4 provides for straight channels that serve as the reaction area, ingress and egress channels, other shapes are possible, e.g., a circular reaction area cut with side inlet and, outlet vents or ports, as well as other configurations, e.g. square, triangular, rectangular, irregular shaped reaction areas, etc. The spacer layer may be fabricated from any convenient material, where representative suitable materials include PET, PETG, polyimide, polycarbonate and the like, where the surfaces of the spacer layer may be treated so as to be adhesive with respect to their respective electrodes and thereby maintain the structure of the electrochemical test strip. Of particular interest is the use of a die-cut double-sided adhesive strip as the spacer layer.

Reaction Zone

As mentioned above, the subject electrochemical test strips include a plurality of reaction zones or areas that are defined by the working electrode, the reference electrode and the spacer layer, where these elements are described above. Specifically, the working and reference electrodes define the top and bottom of the reaction area, while the spacer layer defines the walls of the reaction area. The volume of the reaction area is at least about 0.1 $\mu$l, usually at least about 0.3 $\mu$l and more usually at least about 0.5 $\mu$l, where the volume may be as large as 10 $\mu$l or larger. As mentioned above, each of the reaction areas generally includes at least an inlet port (ingress channel), and in many embodiments also includes an outlet port (egress channel). The cross-sectional area of the inlet and outlet ports may vary as long as it is sufficiently large to provide an effective entrance or exit of fluid from the reaction area, but generally ranges from about $9 \times 10^{-5}$ to $5 \times 10^{-3}$ cm$^2$, usually from about $1.3 \times 10^{-3}$ to $2.5 \times 10^{-3}$ cm$^2$.

In certain embodiments of the invention, each reaction zone or area has its own distinct ingress and egress channel. As such, the number of different ingress channels in these embodiments equals the number of different reaction areas of the strip. In yet other embodiments, two or more of the ingress channels may merge into a single channel prior to exit from the strip (see for example channel 50 of FIG. 2), such that fluid can be introduced into two or more different reaction areas from a single entry port. In other words, a single ingress channel may branch into two or more sub-channels that enter different reaction zones of the strip. The spacer layer of the subject strips is designed to provide for the desired ingress channel pattern, e.g., separate or merged channels.

Present in each of the reaction areas is a reagent composition or system, where the system is necessary or desirable for analyte detection with the strip. In certain embodiments, e.g., multi-use strips, the reagent system is the same in all of disparate reaction areas of the strip, In other embodiments, e.g., where the strip is employed to simultaneously assay for a panel or plurality of different analytes, the reagent composition will differ among the disparate reaction zones or areas. In other words, at least two different reagent compositions will be present in different reaction areas of the strip, where the number of different reagent compositions may be as great as the number of different reaction zones or areas of the strip.

In many embodiments, at least one of the reagent compositions is a redox reagent system, which reagent system provides for the species that is detected by the electrode and therefore is used to derive the concentration of analyte in a physiological sample. The redox reagent system present in the reaction area typically includes at least an enzyme(s) and a mediator. In many embodiments, the enzyme member(s) of the redox reagent system is an enzyme or plurality of enzymes that work in concert to oxidize the analyte of interest. In other words, the enzyme component of the redox reagent system is made up of a single analyte oxidizing enzyme or a collection of two or more enzymes that work in concert to oxidize the analyte of interest. Enzymes of interest include oxidases, dehydrogenases, lipases, kinases, diaphorases, quinoproteins and the like.

The specific enzyme present in the reaction area depends on the particular analyte for which the electrochemical test strip is designed to detect, where representative enzymes include: glucose oxidase, glucose dehydrogenase, cholesterol esterase, cholesterol oxidase, lipoprotein lipase, glycerol kinase, glycerol-3-phosphate oxidase, lactate oxidase, lactate dehydrogenase, pyruvate oxidase, alcohol oxidase, bilirubin oxidase, uricase, and the like. In many preferred embodiments where the analyte of interest is glucose, the enzyme component of the redox reagent system is a glucose oxidizing enzyme, e.g. a glucose oxidase or glucose dehydrogenase.

The second component of the redox reagent system is a mediator component, which is made up of one or more mediator agents. A variety of different mediator agents are known in the art and include: ferricyanide, phenazine ethosulphate, phenazine methosulfate, pheylenediamine, 1-methoxy-phenazine methosulfate, 2,6-dimethyl-1,4-benzoquinone, 2,5-dichloro-1,4-benzoquinone, ferrocene derivatives, osmium bipyridyl complexes, ruthenium complexes and the like. In those embodiments where glucose in the analyte of interest and glucose oxidase or glucose dehydrogenase are the enzyme components, mediator of particular interest is ferricyanide. Other reagents that may be present in the reaction area include buffering agents, e.g. citraconate, citrate, phosphate, "Good" buffers and the like.

The redox reagent system is generally present in dry form. The amounts of the various components may vary, where the amount of enzyme component typically ranges from about 0.1 to 10% by weight.

METHODS

Also provided by the subject invention are methods of using the subject electrochemical test strips to determine the concentration of an analyte, or panel of analytes, in a physiological sample. A variety of different analytes may be detected using the subject test strips, where representative analytes include glucose, cholesterol, lactate, alcohol, and the like. In many preferred embodiments, the subject methods are employed to determine the glucose concentration in a physiological sample. While in principle the subject methods may be used to determine the concentration of an analyte in a variety of different physiological samples, such as urine, tears, saliva, and the like, they are, particularly suited for use in determining the concentration of an analyte in blood or blood fractions, and more particularly in whole blood.

Figure 5:
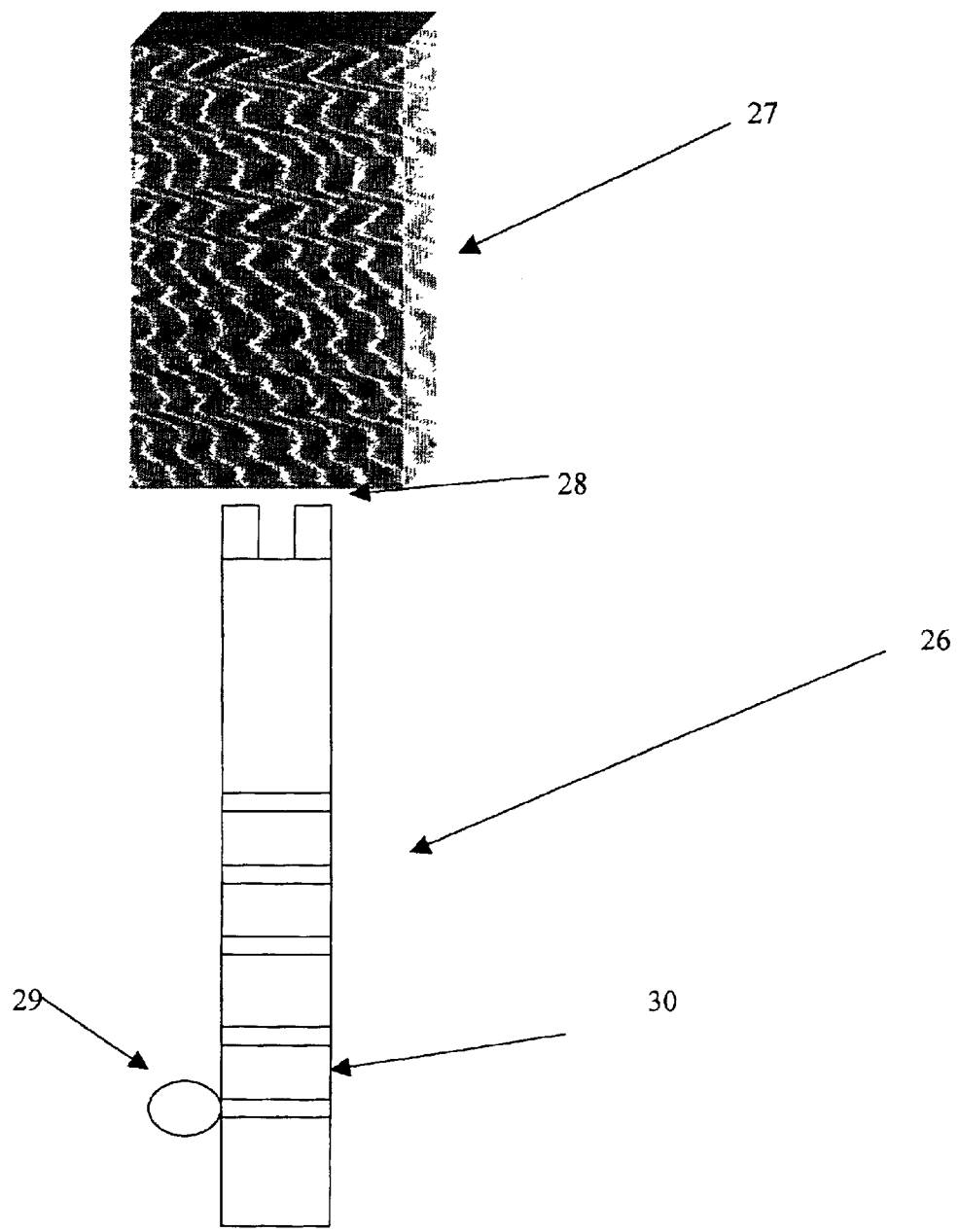
FIG. 5 provides a representation of an electrochemical test strip according to the subject invention in use.

In practicing the subject methods, the first step is to introduce a quantity of the physiological sample into at least one of the reaction areas of the test strip, where the electrochemical test strip is described supra. Generally, the reaction area most proximal to the edge of the strip is employed first. In FIG. 5, the contact 28 of coelectrochemical test strip 26 is depicted being inserted into a electrosensing device 27, and the physiological sample is applied to the very last reaction zone 30 of the strip 26.

The amount of physiological sample, e.g. blood, that is introduced into each reaction area of the test strip may vary, but generally ranges from about 0.1 to 10 µl, usually from about 0.3 to 1.6 µl. The sample may be introduced into the reaction area using any convenient protocol, where the sample may be injected into the reaction area, allowed to wick into the reaction area, and the like, as may be convenient.

In certain embodiments, the strip is employed for sequential analyte detection assays. In these embodiments, sample is introduced into each of the reaction areas at different times.

Following application of the sample to the reaction zone, an electrochemical measurement is made using the reference and working electrodes. The electrochemical measurement that is made may vary depending on the particular nature of the assay and the device with which the electrochemical test strip is employed, e.g. depending on whether the assay is coulometric, amperometric or potentiometric. Generally, the electrochemical measurement will measure charge (coulometric), current (amperometric) or potential (potentiometric), usually over a given period of time following sample introduction into the reaction area. Methods for making the above described electrochemical measurement are further described in U.S. Pat. Nos.: 4,224,125; 4,545,382; and 5,266,179; as well as WO 97//18465; WO 99/49307; the disclosures of which are herein incorporated by reference. If two or more reaction areas are used simultaneously, means are provided for electrically isolating each of the disparate cells.

Following detection of the electrochemical signal generated in the reaction zone as described above, the amount of the analyte present in the sample introduced into the reaction zone is then determined by relating the electrochemical signal to the amount of analyte in the sample. In making this derivation, the measured electrochemical signal is typically compared to the signal generated from a series of previously obtained control or standard values, and determined from this comparison. In many embodiments, the electrochemical signal measurement steps and analyte concentration derivation steps, as described above, are performed automatically by a device designed to work with the test strip to produce a value of analyte concentration in a sample applied to the test strip. A representative reading device, i.e., meter, for automatically practicing these steps, such that the user need only apply sample to the reaction zone and then read the final analyte concentration result from the device, is further described in copending U.S. application Ser. No. 09/333,793 filed Jun. 15, 1999, the disclosure of which is herein incorporated by reference.

Where the reaction zones of the strips are used for different assays, where desired each used reaction area may be separated from the remainder of the strip, e.g., cut away from the strip, following use and prior to use of the next reaction area. This process is illustrated in FIGS. 3 and 4, where cuts 25 are made to the strip to remove each used reaction area prior to use of the next reaction area.

Systems and Kits

Also provided by the subject invention are systems and kits for use in practicing the subject methods. The systems and kits of the subject invention at least include an electrochemical test strip of the subject invention, as described above. The subject systems and kits may further include a means for obtaining a physiological sample. For example, where the physiological sample is blood, the subject systems kits may further include a means for obtaining a blood sample, such as a lance for sticking a finger, a lance actuation means, and the like. In addition, the subject systems kits may include a control solution, e.g. a glucose control solution that contains a standardized concentration of glucose. In certain embodiments, the systems and kits also comprise a meter instrument, as described above, for detecting an electrochemical signal using the electrodes following sample application and relating the detected signal to the amount of analyte in the sample. Finally, the systems and kits may include instructions for using the subject reagent test strips in the determination of an analyte concentration in a physiological sample. These instructions may be present on one or more of the packaging, a label insert, containers present in the kits, and the like.

The subject invention provides for significant improvements in that each strip can be employed multiple times. As such, the subject invention provides for more efficient use of strips and cost savings in terms of decreased waste. In addition, the subject invention provides for the opportunity to test for a panel of analytes using a single strip. As such, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. An electrochemical test strip comprising:
   (a) a plurality of reaction zones defined by opposing working and reference electrodes separated by a spacer layer, wherein each of said reaction zones is defined by a bore through said spacer layer and further wherein each of said reaction zones has its own fluid ingress channel to provide for fluid communication between said reaction zones and the external environment of said test strip; and
   (b) a reagent composition present in each of said reaction zones.

2. The electrochemical test strip according to claim 1, wherein said test strip comprises from 2 to 25 reaction zones.

3. The electrochemical test strip according to claim 1, wherein each of said reaction zones houses the same reagent composition.

4. The electrochemical test strip according to claim 1, wherein at least two of said reaction zones house different reagent compositions.

5. The electrochemical test strip according to claim 1, wherein at least one of said electrodes comprises a material selected from the group consisting of gold, palladium, silver, iridium, carbon, platinum, nichrome, doped indium tin oxide and stainless steel.

6. The electrochemical test strip according to claim 5, wherein said electrode comprises gold or palladium.

7. The electrochemical test strip according to claim 1, wherein each of said reaction zones has a volume ranging from about 0.1 to 10 $\mu$l.

8. The electrochemical test strip according to claim 1, wherein said reference electrode is a gold electrode.

9. The electrochemical test strip according to claim 1, wherein said working electrode is a palladium electrode.

10. The electrochemical test strip according to claim 1, wherein said strip is present in a meter.

11. The electrochemical test strip according to claim 1, wherein at least one of said reagent compositions is a redox reagent system.

12. The electrochemical test strip according to claim 11, wherein said redox reagent system comprises at least one enzyme and a mediator.

13. The electrochemical test strip according to claim 12, wherein said at least one enzyme includes an oxidizing enzyme.

14. The electrochemical test strip according to claim 13, wherein said oxidizing enzyme in a glucose oxidizing enzyme.

15. A method of determining the concentration of an analyte in a physiological sample, said method comprising:
   (a) applying said physiological sample to an electrochemical test strip comprising a plurality of reaction zones defined by opposing working and reference electrodes separated by a spacer layer and a reagent composition present in each of said reaction zones, wherein each of said reactions zones are provided by a bore through said spacer layer and further wherein each of said reaction zones has its own fluid ingress channel to provide for fluid communication between said reaction zones and the external environment of said test strip;
   (b) detecting an electrical signal in said reaction zone using said opposing electrodes; and
   (b) relating said detected electrical signal to the amount of said analyte in said sample.

16. The method according to claim 15, wherein said analyte is glucose.

17. The method according to claim 16, wherein said redox reagent system comprises a glucose oxidizing enzyme.

18. The method according to claim 15, wherein said method comprises employing a meter.

19. A kit for use in determining the concentration of an analyte in a physiological sample, said kit comprising:
   (a) an electrochemical test strip comprising a plurality of reaction zones defined by opposing working and reference electrodes separated by a spacer layer and a reagent composition present in each of said reaction zones, wherein each of said reaction zones are provided by a bore through said spacer layer and further wherein each of said reaction zones has its own fluid ingress channel to provide for fluid communication between said reaction zones and the external environment of said test strip; and
   (b) at least one of;
       (i) a means for obtaining said physiological sample; and
       (ii) an analyte standard.

20. The kit according to claim 19, wherein said means for obtaining said physiological sample is a lance.

21. The kit according to claim 19, wherein said kit further comprises a meter.

22. A system for use in determining the concentration of an analyte in a physiological sample, said system comprising:
   (a) an electrochemical test strip comprising a plurality of reaction zones defined by opposing working and reference electrodes separated by a spacer layer and a reagent composition present in each of said reaction zones, wherein each of said reaction zones are provided by a bore through said spacer layer and further wherein each of said reaction zones has its own fluid ingress channel to provide for fluid communication between said reaction zones and the external environment of said test strip; and
   (b) a meter.

23. The system according to claim 22, wherein said system further comprises a means for obtaining said physiological sample.

24. The system according to claim 22, wherein said system further comprises an analyte standard.

25. An electrochemical test strip comprising:

a plurality of reaction zones defined by opposing working and reference electrodes separated by a spacer layer, wherein each of said reaction zones is defined by a bore through said spacer layer and further wherein at least two of said reaction zones have fluid ingress channels that merge to produce a single ingress channel to provide for fluid communication between said reaction zones and the external environment of said test strip; and (b) a reagent composition present in each of said reaction zones.

26. The electrochemical test strip according to claim 25, wherein said test strip comprises from 2 to 25 reaction zones.

27. The electrochemical test strip according to claim 25, wherein each of said reaction zones houses the same reagent composition.

28. The electrochemical test strip according to claim 25, wherein at least two of said reaction zones house different reagent composition.

29. The electrochemical test strip according to claim 25, wherein at least one of said reagent compositions is a redox reagent system.

30. The electrochemical test strip according to claim 29, wherein said at least one enzyme includes an oxidizing enzyme.

31. The electrochemical test strip according to claim 30, wherein said oxidizing enzyme is a glucose oxidizing enzyme.

32. A method of determining the concentration of an analyte in a physiological sample, said method comprising:

(a) applying said physiological sample to an electrochemical test strip comprising a plurality of reaction zones defined by opposing working and reference electrodes separated by a spacer layer and a reagent composition present in each said reaction zones, wherein each of said reactions zones are provided by a bore through said spacer layer and further wherein at least two of said reaction zones have fluid ingress channels that merge to produce a single ingress channel to provide for fluid communication between said reaction zones and the external environment of said test strip;

(b) detecting an electrical signal in said reaction zone using said opposing electrodes;

(c) relating said detected electrical signal to the amount of said analyte in said sample.

33. A kit for use in determining the concentration of an analyte in a physiological sample, said kit comprising:

(a) an electrochemical test strip comprising a plurality of reaction zones defined by opposing working and reference electrodes separated by a spacer layer and a reagent composition present in each of said reaction zones, wherein each of said reaction zones are provided by a bore through said spacer layer and further wherein at least two of said reaction zones have fluid ingress channels that merge to produce a single ingress channel to provide for fluid communication between said reaction zones and the external environment of said test strip; and (b) at least one of:

(i) a means for obtaining said physiological sample; and (ii) an analyte standard.

34. A system for use in determining the concentration of an analyte in a physiological sample, said system comprising:

(a) an electrochemical test strip comprising a plurality of reaction zones defined by opposing working and reference electrodes separated by a spacer layer and a reagent composition present in each of said reaction zones, wherein each of said reaction zones are provided by a bore through said spacer layer and further wherein at least two of said reaction zones have fluid ingress channels that merge to produce a single ingress channel to provide for fluid communication between said reaction zones and the external environment of said test strip; and (b) a meter.

* * * * *